US00PP08314P

United States Patent [19]

Vletter

[11] Patent Number: Plant 8,314

[45] Date of Patent: Jul. 20, 1993

[54] LILY PLANT NAMED BERLIN

[75] Inventor: Floris Vletter, Rijnsburg, Netherlands

[73] Assignee: Gebr. Vletter & J.A. Den Haan, Rijnsburg, Netherlands

[21] Appl. No.: 796,695

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A lily plant named Berlin, characterized by its light pink main flower color, cherry red streaking along the midvein of each tepal, red-purple spot markings, very upright flower position and its floriferous habit.

1 Drawing Sheet

The present invention comprises a new and distinct cultivar of lily, botanically known as Lilium, known commercially as Lilium oriental hybrid, and hereinafter referred to by the cultivar name Berlin. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars with good forcing characteristics so as to produce many flowers at minimal bulb size.

The new cultivar was originated from a hybridization made by the inventor in a controlled breeding program in Rijnsburg, The Netherlands in 1981. The female parent was the cultivar Stargazer. The male parent was an unnamed seedling.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying in the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of Berlin which in combination distinguish this lily as a new and distinct cultivar.

1. A distinctive light pink main flower color;
2. Streaking or striping which is cherry red in color along each midvein, to near the tip of the tepal;
3. Many red-purple spot markings on each tepal;
4. Very upright flower position;

5. Very floriferous habit.

Of the many commercial cultivars known to the present inventor, the most similar in comparison to the new cultivar is Stargazer. In comparison to Stargazer, Berlin has more flowers for the same bulb size, lighter pink flower color with red striping in the center of the tepal, and longer stems. Berlin generally produces 1 to 2 more flowers than Stargazer at the same bulb size. Berlin bulbs measuring approximately 16 centimeters produce 5 to 7 flowers. When flowering is forced under natural light, Berlin produces an inflorescence approximately 9 days earlier than Stargazer, grown under the same conditions. Berlin is fertile.

The accompanying color photographic drawing shows typical flower characteristics of the new cultivar, with colors being as true as possible with illustrations of this type. The photograph comprises a front perspective view showing several flowers open and numerous buds in various stages.

In the following description, color references are made to The Royal Horticultural Society (R.H.S.) Color Chart. The color values were determined at Wageningen in 1988–1989 and at Rijnsburg in July 1991.

Origin: Seedling from Breeding Program.

Parentage:

*Seed parent.*—Stargazer.

*Pollen parent.*—Unnamed seedling.

Classification:

*Botanical.*—Lilium.

*Commercial.*—Oriental hybrid.

THE PLANT

Form: A single stem carrying numerous pedicels alternately arranged.

Height: Medium to tall; height is approximately 120 cm on opening of anthers of first flower.

Growth habit: Vigorous.

Stem: 144B in color; circular in transverse section; internodal length uniform (2 cm); anthocyanin pigmentation present.

Foliage:

*Quantity.*—40–50 leaves, depending on growing conditions.

*Size of leaf.*—Mature leaves are medium in length (18 cm); width is medium (3.5 cm).

*Shape of leaves.*—Generally ovate.

*Texture.*—Smooth with weak glossiness; no pubescence on lower side.

*Color.*—Medium green 137A.

Bulbs:

*Size.*—Outlet 6-30 cm.

*Color.*—Purplish brown.

Roots: Both stem and contractile present.

THE BUD

Form: Tapering (like a lancet).

Size: 10-11 cm in length.

Opening: Unfolds normally.

Color: Light yellow (color prior to opening) with light pink stripe.

Tepals: Folded, three visible.

THE FLOWER

Blooming habit: Raceme.

Size: Approximately 21 cm in total diameter depending on growing conditions.

Borne: Upright.

Shape: Generally in form of hexagonal star; bowl shaped in cross-section.

Tepalage:

*Number of tepals.*—Six.

*Arrangement.*—Three inner and three outer; each with marginal undulation.

*Color.*—Upper surface: Light purple 65C.
Lower surface: White 155D with tinge of purple 65D.

*Spotting or marking.*—Dark red purple spots, each of which is about 1-3 mm in diameter, yellow to green colored strip at base of each tepal.

Nectaries and papillae: Present; strong.

Pedicel:

*Length.*—13 cm (first flower).

*Color.*—Medium green with anthocyan pigmentation.

*Form.*—Slightly curved.

Texture: Strong papillose.

Disease resistance: No disease problems noted to date.

Fragrance: Present; medium strong.

Lasting quality: Excellent.

REPRODUCTIVE ORGANS

Stamens, anthers:

*Arrangement.*—Anthers form a generally circular pattern.

*Length.*—Medium (8.5 cm).

*Number.*—Six.

*Filaments.*—Light green.

Pollen color: Light brown to orange brown.

Anther color: Purple.

Pistils: One with green style; total length of pistil is 12 cm.

Stigma: Purple stigma.

Ovaries: Triangular in shape; other characteristics typical of oriental lily varieties.

I claim:

1. A new and distinct cultivar of lily plant named Berlin, as illustrated and described.

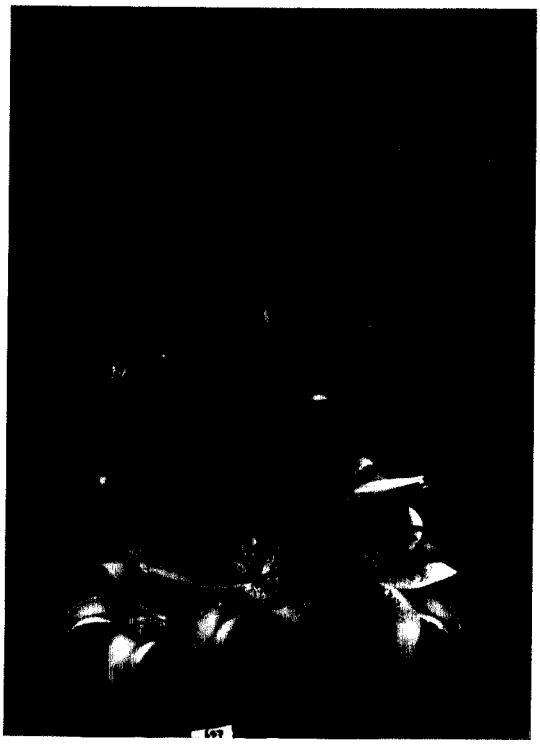

* * * * *